United States Patent
Toker et al.

(10) Patent No.: US 7,294,825 B2
(45) Date of Patent: Nov. 13, 2007

(54) FABRY-PEROT RESONATOR APPARATUS AND METHOD INCLUDING AN IN-RESONATOR POLARIZING ELEMENT

(75) Inventors: Gregory Toker, Jerusalem (IL); Andrei Brunfeld, Cupertino, CA (US); Bryan Clark, Mountain View, CA (US)

(73) Assignee: Xyratex Technology Limited, Havant, Hampshire (GB)

( * ) Notice: Subject to any disclaimer, the term of this patent is extended or adjusted under 35 U.S.C. 154(b) by 232 days.

(21) Appl. No.: 11/149,094

(22) Filed: Jun. 8, 2005

(65) Prior Publication Data

US 2005/0232330 A1 Oct. 20, 2005

Related U.S. Application Data

(63) Continuation-in-part of application No. 10/644,243, filed on Aug. 20, 2003, now Pat. No. 7,022,978.

(60) Provisional application No. 60/578,112, filed on Jun. 8, 2004.

(51) Int. Cl.
  *H01J 3/14* (2006.01)
  *H01J 40/14* (2006.01)
  *H01J 5/16* (2006.01)
(52) U.S. Cl. .................. 250/234; 250/216; 359/517
(58) Field of Classification Search ............. 250/201.5, 250/216, 225, 559.11, 559.22, 559.4, 559.45; 356/5.14, 453, 487, 491–495, 237.2; 359/237–324
See application file for complete search history.

(56) References Cited

U.S. PATENT DOCUMENTS

| | | | |
|---|---|---|---|
| 5,235,192 A | 8/1993 | Chase et al. | |
| 6,522,471 B2 | 2/2003 | Clark | |
| 6,653,649 B2 | 11/2003 | Clark et al. | |
| 6,700,840 B2 | 3/2004 | Clark | |
| 6,714,295 B2 | 3/2004 | Clark et al. | |
| 6,717,707 B2 | 4/2004 | Clark | |

(Continued)

OTHER PUBLICATIONS

U.S. Appl. No. 11/143,018, filed Jun. 1, 2005, Brunfeld et al.

(Continued)

*Primary Examiner*—Patrick J. Lee
(74) *Attorney, Agent, or Firm*—Mitch Harris, Atty at Law, LLC; Andrew M. Harris

(57) ABSTRACT

A Fabry-Perot resonator apparatus and method including an in-resonator polarizing element improves detection/measurement sensitivity of an optical system, provides both fields at a single end of the resonator, and overcomes other structural and performance limitations of particular optical systems. A polarizing element, which may be a quarter-wave plate, a 45-degree Faraday rotator or other polarizing element capable of converting between linear and circular polarizations and back, is placed in the resonance path of the Fabry-Perot resonator. The polarizing element effectively doubles the cavity length and orthogonally isolates forward from reverse reflection rays within the resonator, eliminating interference between rays and providing isolated bright and dark fields at each end of the resonator. The polarizing element is introduced in a lens-incorporating Fabry-Perot resonator to eliminate cross-talk between image points and is used in a non-normal incidence Fabry-Perot resonator to emit bright and dark resonance information at either end of the resonator.

22 Claims, 7 Drawing Sheets

U.S. PATENT DOCUMENTS

| | | |
|---|---|---|
| 6,778,307 B2 | 8/2004 | Clark |
| 6,879,421 B2 | 4/2005 | Clark et al. |
| 6,927,864 B2 | 8/2005 | Clark et al. |
| 7,022,978 B2 | 4/2006 | Clark et al. |
| 7,102,740 B2 | 9/2006 | Clark et al. |
| 2005/0218350 A1* | 10/2005 | Brunfeld et al. ....... 250/559.11 |
| 2005/0225775 A1* | 10/2005 | Brunfeld et al. ............ 356/519 |
| 2005/0279954 A1* | 12/2005 | Brunfeld et al. ....... 250/559.11 |

OTHER PUBLICATIONS

U.S. Appl. No. 11/169,517, filed Jun. 29, 2005, Brunfeld et al.
U.S. Appl. No. 11/167,807, filed Jun. 27, 2005, Brunfeld et al.
U.S. Appl. No. 11/156,309, filed Jun. 17, 2005, Brunfeld et al.
U.S. Appl. No. 10/770,866, filed Feb. 4, 2004, Brunfeld et al.

* cited by examiner

FABRY-PEROT RESONATOR APPARATUS AND METHOD INCLUDING AN IN-RESONATOR POLARIZING ELEMENT

CROSS-REFERENCE TO RELATED APPLICATIONS

This application is related to U.S. Provisional Patent Application "DETECTION OF TRANSMISSION FRINGES IN A REFLECTIVE RESONATOR", Ser. No. 60/578,112, filed by the same inventors on Jun. 8, 2004, from which benefit under 35 U.S.C. §119(e) is claimed. The present application is also a Continuation-in-Part of U.S. patent application Ser. No. 10/644,243 entitled "METHOD AND APPARATUS INCLUDING IN-RESONATOR IMAGING LENS FOR IMPROVING RESOLUTION OF A RESONATOR-ENHANCED OPTICAL SYSTEM", which was filed on Aug. 20, 2003 now U.S. Pat. No. 7,022,978 having at least one common inventor and assigned to the same assignee, the specification of which is incorporated by reference.

The present application is also related to co-pending U.S. patent application Ser. No. 11/143,018, entitled "FABRY-PEROT RESONATOR APPARATUS AND METHOD FOR OBSERVING LOW REFLECTIVITY SURFACES" filed on Jun. 1, 2005 by the same inventors and assigned to the same assignee, the specification of which is incorporated herein by reference.

BACKGROUND OF THE INVENTION

1. Field of the Invention

This invention relates to optical systems, and more specifically, to an optical system incorporating a polarizing element within a Fabry-Perot resonator to improve performance of the system.

2. Description of the Related Art

Resonator-enhanced optical inspection systems, storage devices and other optical systems, such as those described by U.S. Pat. Nos. 6,653,649, 6,700,840, 6,714,295, 6,717,707, 6,778,307 issued to Applicant Clark and others, the specifications of which are incorporated herein by reference, provide improved resolution, surface detection and other performance improvements in traditional optical systems and provide new types of optical systems that were not available prior to the inventions disclosed therein. Specifically, the incorporation of a Fabry-Perot resonator in the above-mentioned optical systems has increased the sensitivity of a particular measurement parameter via the resonance effects, and further made it possible to detect certain optical conditions using an intensity detector, whereas an external interferometer was previously required for the measurement.

When incorporating a Fabry-Perot resonator into such systems, often the only available external measurement location is the point of introduction of the illumination beam. In particular, where the Fabry-Perot resonator is formed by a partially reflective surface interacting with the surface to be measured, which might be reflective and not transmissive, then transmission through the resonator is not measurable at all. The only available measurement point is at the partially reflective surface and therefore only the reflection from the Fabry-Perot resonator can be measured.

Intensity measurements of the reflection are much more difficult and prone to error than transmission measurements. Because the field is "bright" between the resonances (i.e., the cavity re-radiates all wavelengths other than the resonant wavelengths), the background level is a function of the mirror efficiencies (reflectivity and absorption) and the power of the input beam. For relative intensity measurements, use of the reflected beam requires measuring a typically non-zero resonance value lower than the background and comparing it to the above-described bright value, which is referred to as "bright field" detection. Transmission measurements are much simpler in that the values between the resonances are near zero and the resonance peak "bright" values are more easily compared to other values near resonance, which is referred to as "dark field" detection.

Further, when the detection and illumination beams are co-located or overlapped at a partially-reflective surface of a modified Fabry-Perot resonator and the illumination and detection areas are imaged onto each other, such as in the lens-incorporating resonator of the above-incorporated parent U.S. patent application, cross-talk between reflections across the image will affect performance unless measures are taken to ensure that the reflections do not interfere.

It would therefore be desirable to improve the performance of the Fabry-Perot resonator-enhanced optical systems disclosed in the above-referenced U.S. Patents, as well as other optical systems, in order to further improve their resolution and performance. It would further be desirable to provide a mechanism for observing a resonance value in a dark field (i.e., bright resonance on dark background) at the illumination input to the resonator. It would also be desirable to provide a mechanism whereby illumination and detection beams can co-located and still yield ideal resonator performance without perfect optics and illumination.

SUMMARY OF THE INVENTION

The above objectives of improving the performance of Fabry-Perot resonator enhanced optical systems as well as adding bright resonance signal observation capabilities at the illumination input of a Fabry-Perot resonator is provided in a Fabry-Perot resonator method and apparatus incorporating a polarizing element. The method and apparatus further overcome cross-talk interference when illumination and detection beams are co-located or overlapped and imaged onto one another in the resonator.

The polarizing element changes a polarization state of a resonant reflection twice during a round-trip path through the resonator, so that orthogonal polarization states are maintained between the terminal reflections in the Fabry-Perot resonator. The action of the polarizing element thereby doubles the effective cavity length of the Fabry-Perot resonator, increasing the sensitivity of the resonator and providing availability of both a "bright" and "dark" field output from the resonator at the illumination input point (and alternatively at a transmission output point).

The polarizing element can be a quarter-wave plate, a 45-degree Faraday rotator or other element capable of converting a ray between linear and circular polarization on one pass through the resonator and back to linear polarization (of an orthogonal direction) on the return reflection.

The detection and illumination beams can be co-located and their spots imaged onto each other at a partially reflective surface while preserving ideal performance in the Fabry-Perot resonator, because the opposite image sides are orthogonally polarized at the points of reflection and therefore do not interfere.

If direction-changing optics are incorporated within the resonator, so that a surface of interest may be included in the resonant path at a non-normal incidence angle, as described in the above-incorporated Patent Application "FABRY-PEROT RESONATOR APPARATUS AND METHOD FOR OBSERVING LOW REFLECTIVITY SURFACES", then the already-doubled sensitivity results in a quadrupled sensitivity with the introduction of the polarizing element.

The foregoing and other objects, features, and advantages of the invention will be apparent from the following, more particular, description of the preferred embodiment of the invention, as illustrated in the accompanying drawings, wherein like reference numerals indicate like elements.

DETAILED DESCRIPTION OF ILLUSTRATIVE EMBODIMENT

Figure 1:
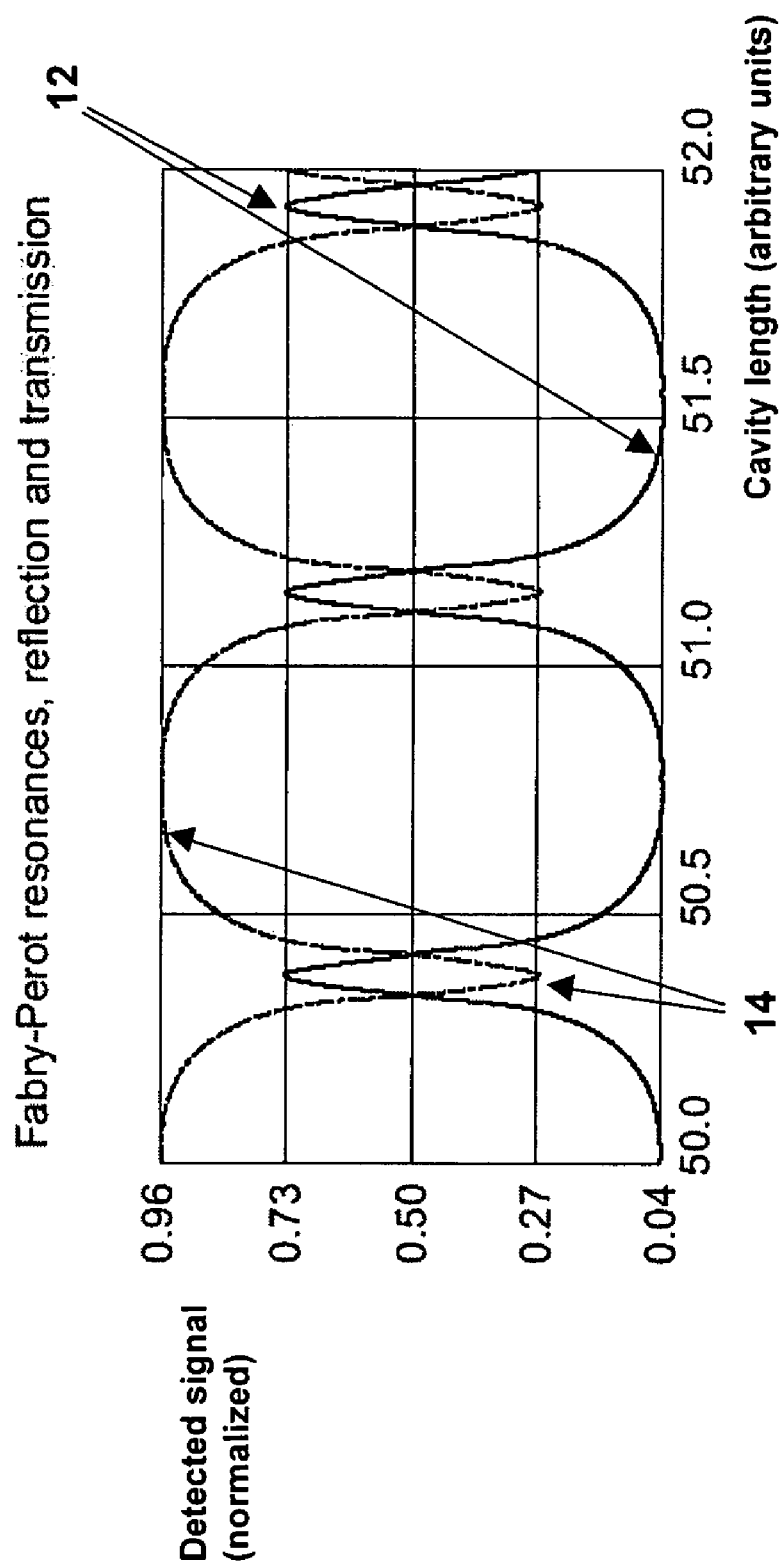
FIG. 1 is a graph showing Fabry-Perot resonator behavior versus cavity length.

The above-incorporated U.S. Patents describe various resonator-enhanced optical systems, such as optical storage data and retrieval systems having improved data density, optical measurement systems having improved resolution and contrast, and optical systems having improved detector phase/amplitude slope characteristics controlled over portions of the detector response. The improvements above-incorporated U.S. Patents are developed by placement and tuning of resonators within the optical paths of the associated systems.

The parent Application include further refinements to resonators and resonator-enhanced optical systems to include lenses for mapping region to region on the resonator reflector(s) and surface of interest to improve surface feature detection performance and desensitize the resonator to variations in positioning and aberrations in the optical components, as well as surface variations that are not being detected, such as inclination.

The above-incorporated Patent Application entitled "FABRY-PEROT RESONATOR APPARATUS AND METHOD FOR OBSERVING LOW REFLECTIVITY SURFACES", details changes to resonator structures and optical systems that permit angles of incidence other than normal for interacting with the surface of interest, in order to measure low-reflectivity surfaces.

The present invention concerns a method and resonator apparatus that incorporate a polarizing element within a Fabry-Perot resonator that provides a variety of benefits with respect to the above-mentioned optical systems. The result of the introduction of a polarizing element in the resonant path of a Fabry-Perot resonator is to cause a reflection incident on one of the reflective surfaces of the resonator to be orthogonally polarized to the corresponding return reflection. Because the terminal reflections of the resonance are orthogonal at each reflector for a full pass through the resonator, they will not interfere until another trip is made through the resonator, doubling the effective cavity length of the resonator and thus doubling the sensitivity.

Also, because odd-order reflections are effectively isolated from even-order reflections of the resonator, and that two orthogonal polarizations are present at each reflector, selection of one polarization for detection provides for either dark or bright resonance patterns at either the reflection end or the transmission end of the Fabry-Perot resonator. If both polarizations are detected, then complete information about polarization states in the cavity and therefore at the surface of interest are detected. If an inclined resonance path is provided at the surface of interest, then information about reflectivity of each polarization can be determined.

Finally, the challenges of maintaining a system free from cross-talk in lens-incorporating resonator systems and other systems in which the incident beam is co-located or overlaps the detection beam are alleviated by providing a mechanism for isolating the incident beam from the reflections via the change in polarization.

Referring now to FIG. 1, the response of a Fabry-Perot resonator is depicted for both bright resonance (or dark field resonance pattern) 12 and dark resonance pattern (or bright field resonance pattern) 14, corresponding respectively to transmission through the resonator and reflection from the resonator, respectively. It is clear from the graph that the bright field resonance pattern 14 is more difficult to measure with respect to the amplitude of the peaks of pattern 14 than the dark field resonance pattern 12 which has a near-zero background level, permitting possible direct comparison of intensity values (essentially ignoring the background value) and giving an effectively larger dynamic range (effectively 150:1 vs. 3:1 in the diagram for bright resonance versus dark resonance, respectively).

Figure 2:
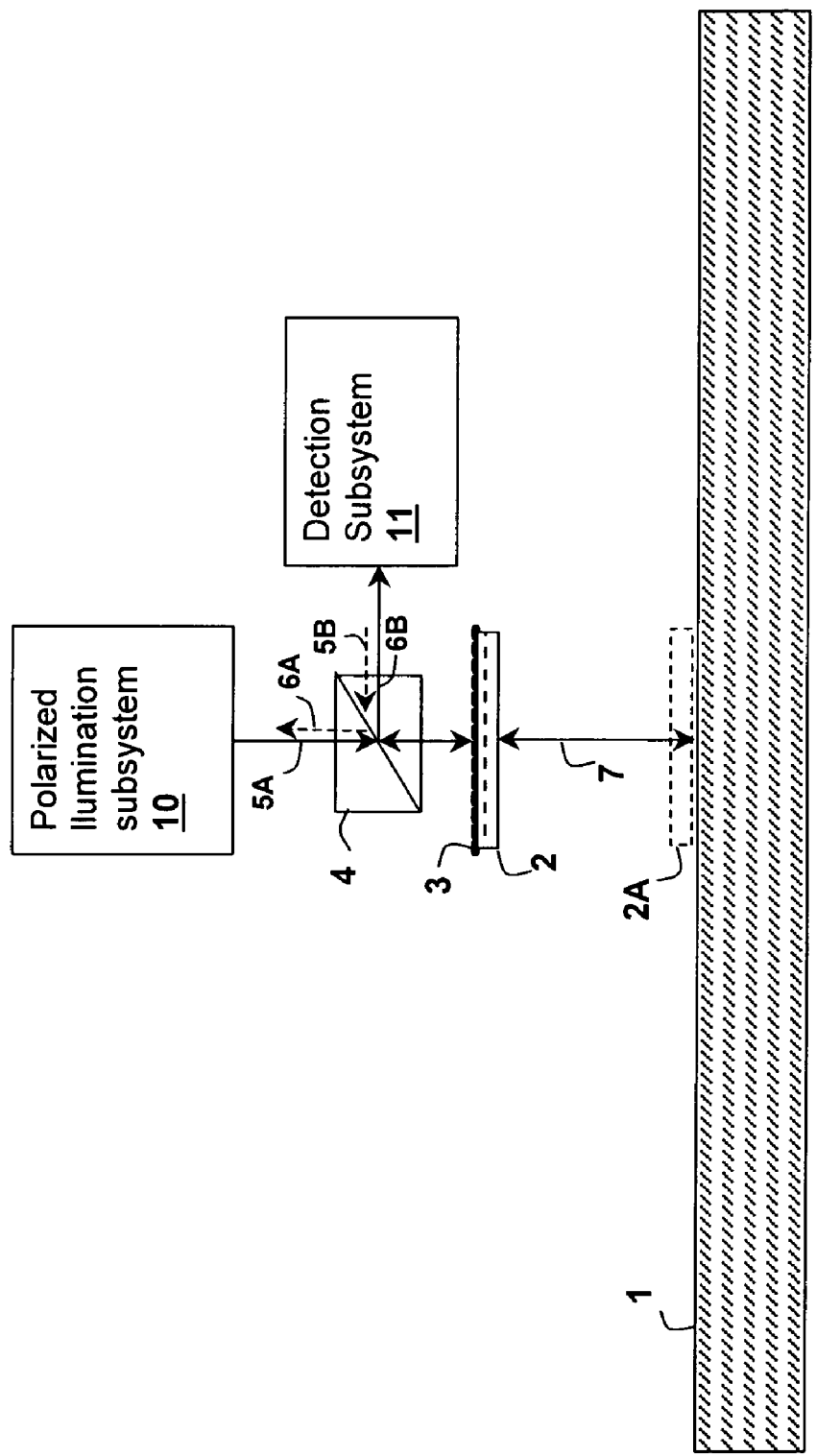
FIGS. 2-7 are pictorial diagrams depicting optical systems in accordance with various embodiments of the invention.

With reference now to FIGS. 2-7, the invention will be illustrated, and particularly with respect to FIG. 2 an optical schematic of a resonator-enhanced optical system in accordance with an embodiment of the invention is illustrated. Resonance is supported between a partially reflective surface 3 and a surface of interest 1 with a resonance path extending along ray 7. Between partially reflective surface 3 and surface of interest 1, a polarizing element 2 is inserted. Polarizing element 2 is adjusted to convert linear polarized light to circular polarized light. Suitable structures are a quarter-wave plate oriented at 45 degrees or a 45-degree Faraday rotator.

A polarized illumination subsystem 10, which may be a laser with inherent linear polarization or another illumination source with a polarizing element at the output is used to provide an illumination beam 5A that is introduced through polarizing beam splitter 4 in a direction and input polarization oriented according to the polarization of the illumination source, to transmit light from illumination beam 5A into the cavity formed between partially reflective surface 3 and surface of interest 1. Without polarizing element 2 a Fabry-Perot resonator would be formed between partially reflective surface 3 and surface of interest 1, with each reflection along ray 7 interfering at the endpoints of the resonator (i.e., partially reflective surface 3 and surface of interest 1), so that resonances occur when the cavity length is a multiple of one-half of a wavelength. However, polarizing element 2 isolates every other reflection, as each pass through polarizing element 2 results in a shift around the pattern LP(P)→RHCP→LP(S)→LHCP (or an equivalent other sequence) where LP(P) is parallel linear polarization, LP(S) is linear perpendicular polarization, RHCP is right-hand circular polarization and LHCP is left-hand circular polarization. Thus, a ray passing through polarizing element 2 to surface of interest 1 and back to partially-reflective surface 3 does not interfere with itself, because of the orthogonal polarization. Four passes are required through polarizing element 2 before a reflection will interfere with itself at partially reflective surface 3 or surface of interest 1, generating resonances at multiples of one quarter wavelength and increasing the sensitivity of the resonator.

A detection subsystem 11 is shown receiving light 6B coupled in the orthogonal polarization with respect to the illumination polarization out of polarizing beam splitter 4.

The pattern of the light output 6B is that of dark field detection, even though detection subsystem 11 is located at the illumination end of the resonator (there is no transmission end available in the current embodiment). The bright field output could additionally be observed by equipping the system with an additional or alternative detector to detect the intensity of beam 6A that is returned along the illumination path, or alternatively, illumination could be applied at illumination path 5B instead of path 5A to make the same pattern change. In both cases, the observation of the bright field fringes would be performed by an additional non-polarizing beam splitter (not shown).

The optical system illustrated in FIG. 2 is one of the structurally simplest embodiments of the present invention, but still benefits from the action of polarizing element 2 due to the selectability of dark or bright field detection (or both for comparison) at the illumination input of the resonator. The depicted embodiment also benefits from increased sensitivity due to the effective increase in cavity length provided by the presence of polarizing element 2. For all embodiments of the invention, it is generally possible to relocate polarizing element 2 to alternate positions within the resonance path of the resonator. For example, optional alternate polarizing element position 2A would provide the same increase in sensitivity and the same ability to select the alternate resonance pattern (dark field instead of bright field).

Figure 3:
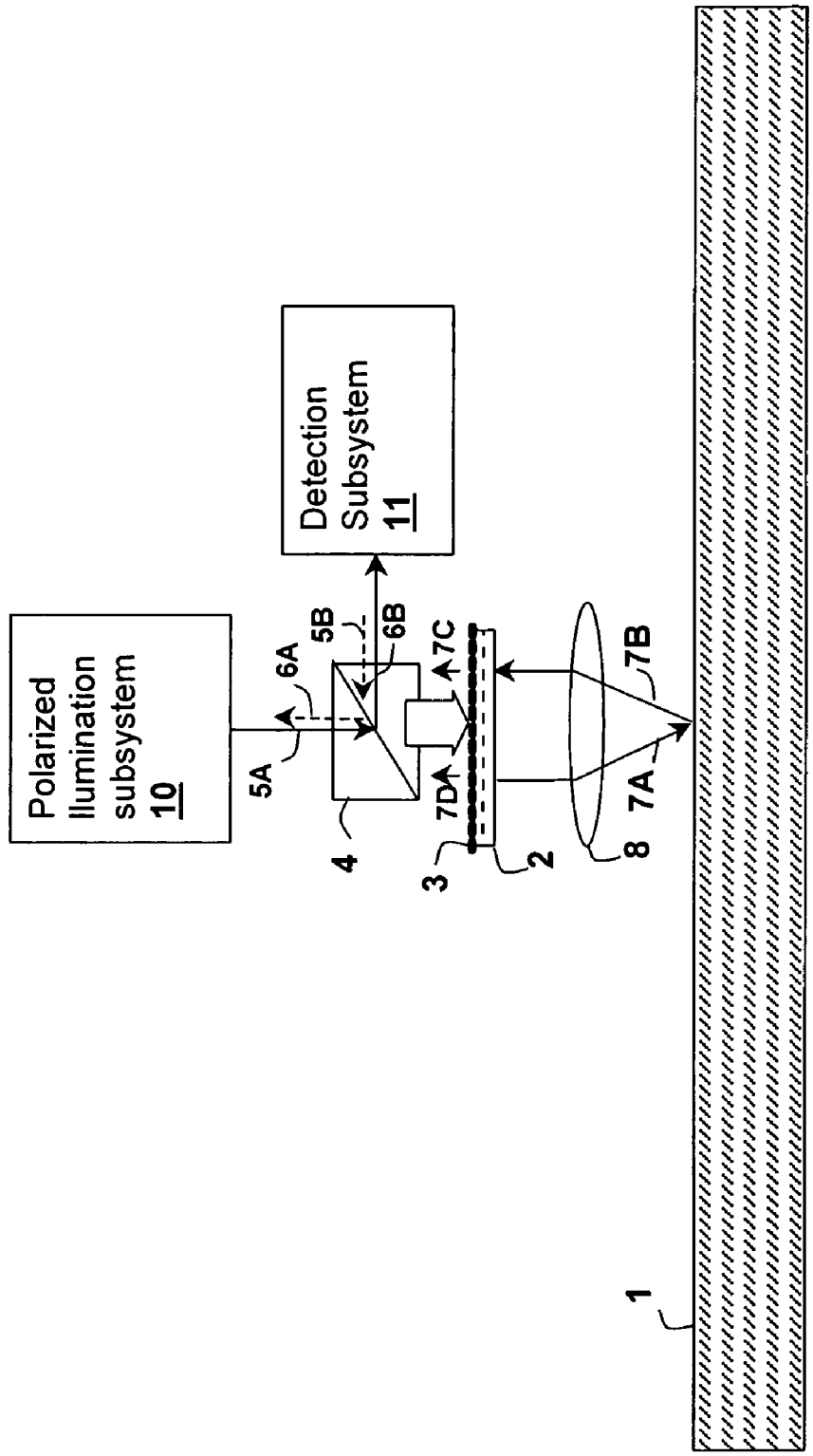

Referring now to FIG. 3, another benefit of the present invention with respect to lens-enhanced resonator systems is illustrated in accordance with an embodiment of the present invention. The optical system of FIG. 3 operates in a manner very similar to the embodiment depicted in FIG. 2, so only differences shall be described in detail below. A lens 8 or lens system in the resonator is provided within the resonator formed by partially reflective surface 3 and surface of interest 1 that images a region of surface of interest 1 on partially reflective surface 3. Generally, a large area on partially reflective surface 3 will be imaged to a point on surface of interest 1, with a finite conjugation ratio or focused onto surface of interest 1 with an infinite conjugation ratio, so that variations in partially reflective surface 3 have a lowered effect on resonance performance, while resolution and sensitivity at surface of interest 1 are maximized. Without polarizing element 2, light ray 7A passes from partially reflective surface 3 through lens 8 reflects from surface of interest 1 and returns to partially reflective surface 3 as ray 7B. For any point on partially reflective surface 3 that is imaged through lens 8, return ray 7B would pass partially reflective surface 3 as ray 7C and interfere with the illumination (shown as the wide arrow to illustrate the finite width of the beam). However, polarizing element 2 provides a benefit (in addition to the increased sensitivity mentioned above) in that ray 7C is orthogonal in polarization to the incident illumination and therefore does not interfere with the illuminating beam. The same is true for the ray that initiates backward along the line of path taken by ray 7B and returns along the line of path taken by ray 7A as ray 7D. The above described cross-coupling could generate instabilities in the resonator. Polarizing element 2 greatly improves the performance of the resonator formed between partially reflective surface 3 and surface of interest 1 by reducing or eliminating cross-coupling between the illumination and the inverted field returned through lens 8 that would otherwise interfere.

Figure 4:
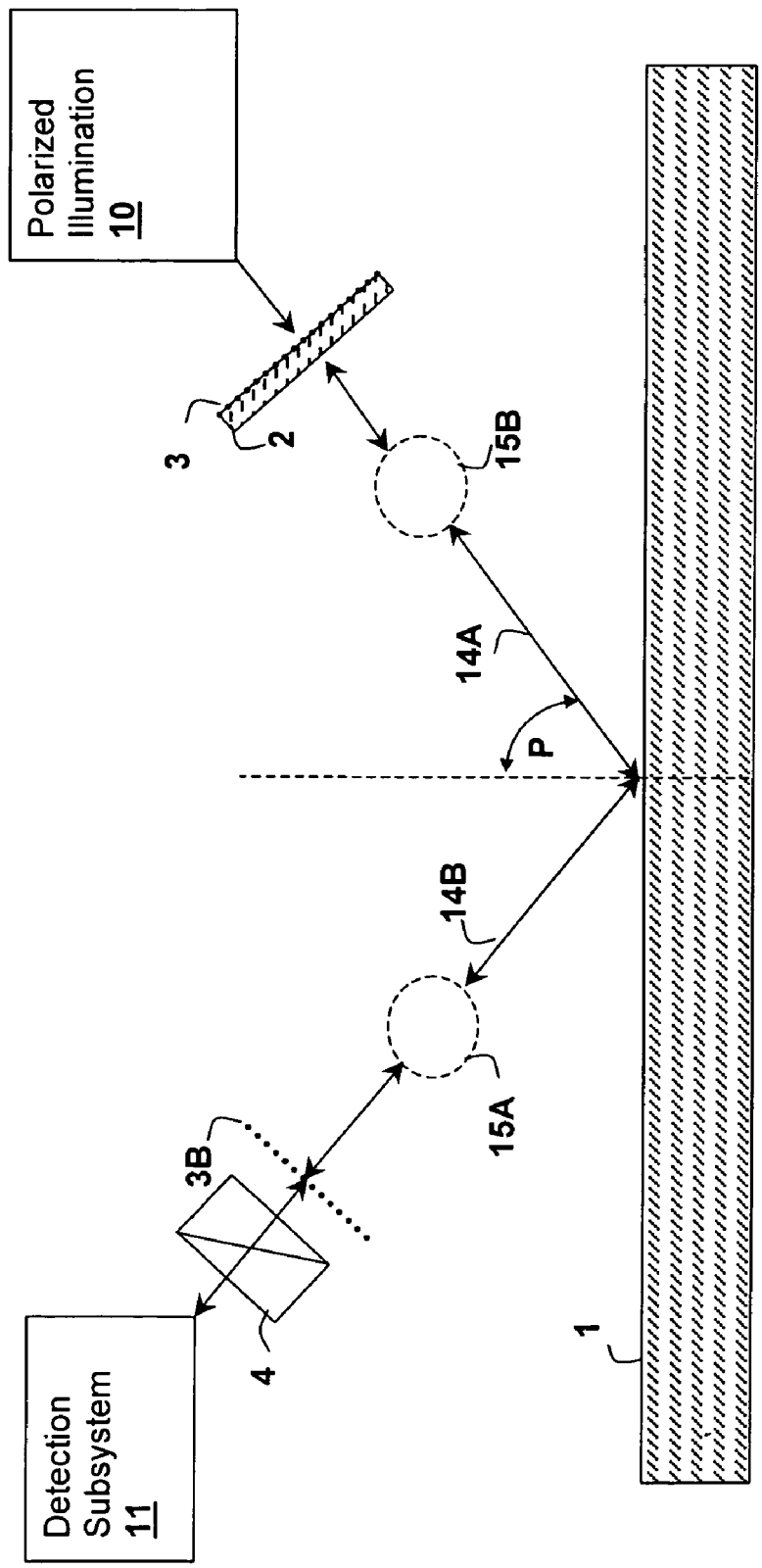

Referring now to FIG. 4 a three-reflector Fabry-Perot measurement system of a type similar to that disclosed in the above-incorporated U.S. Patent Application "FABRY-PEROT RESONATOR APPARATUS AND METHOD FOR OBSERVING LOW REFLECTIVITY SURFACES" is shown. The structure of the system of FIG. 4 differs from the above-described Fabry-Perot resonators in that the resonance optical path 14A, 14B intersects surface of interest 1 at an angle P away from normal by orienting first partially reflective surface 3 and a second partially reflective surface 3B at angles such that the resonance path is established at the non-normal angle P with respect to surface of interest 1, while the intersection of the resonance path with partially reflective surfaces 3 and 3B is at the normal angle. The depicted system is particularly useful in that by changing the angle of incidence of the resonance optical path upon surface of interest, surfaces having a lower than desirable reflectivity can be measured more effectively, as reflectivity generally changes with the angle of incidence. Such orientations also have value any time angle-of-incidence-specific information needs to be obtained such as reflectivity as a function of angle.

Focusing systems or lenses 15A and 15B, may be optionally included to improve resolution of the system by imaging or focusing as described above with respect to the embodiment of FIG. 3. Polarizing element 2 is shown adjoining partially reflective surface 3, but may be positioned anywhere along the resonance path, including at surface of interest 1, such as when polarizing element 2 is a coating on surface of interest 1. Attention must be paid to the position of polarizing element 2 with respect to the illumination polarization at the surface of interest 1, as the polarization at the surface of interest will change depending on whether polarizing element 2 is in the illumination portion of the resonance path (i.e., between partially reflective surface 3 and surface of interest 1). In particular, due to the non-normal incidence of resonance path 14A on surface of interest 1, the illumination polarization is critical to the reflectivity and will be circular polarization if illumination system 10 provides linear polarization and vice-versa.

Polarizing beam splitter 4 is oriented properly to receive a beam exiting the cavity at partially reflective surface 3B and can be used to detect one or both polarizations as described above with respect to the other embodiments. Detection subsystem 11 provides the detection output of the system, which is generally an electronic signal measure of intensity of light detected at one or more detectors.

Figure 5:
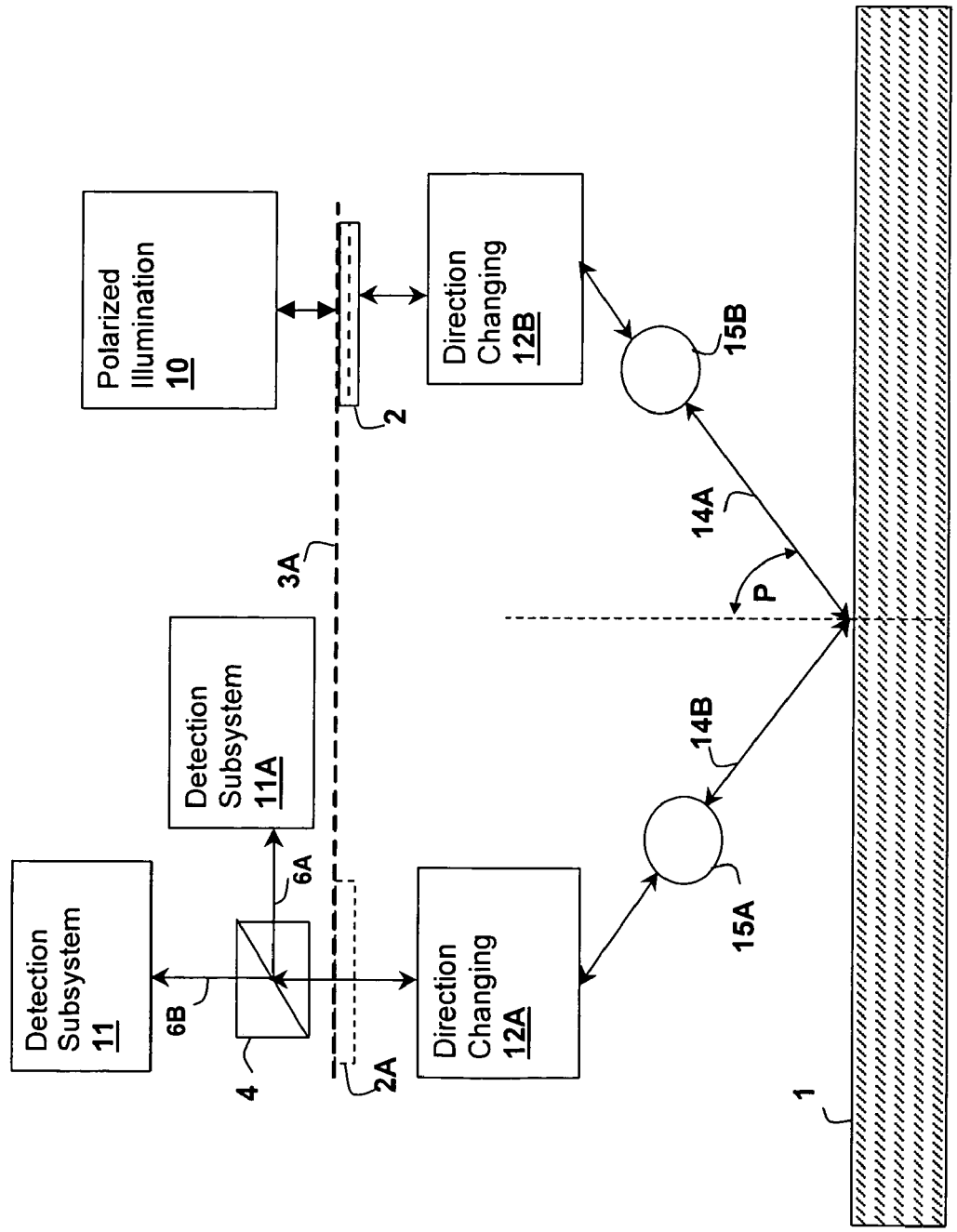

Referring now to FIG. 5 another triple-reflector Fabry-Perot measurement system of a type similar to that disclosed in the above-referenced U.S. Patent Application. The structure of the system of FIG. 5 differs from the above-described Fabry-Perot system of FIG. 4 in that the resonance optical path 14A, 14B intersects surface of interest 1 at an angle P away from normal by virtue of two direction changing elements 12A, 12B such as those described in the above-referenced U.S. patent application. For example, prisms, a high-index lens fed and detected off-axis, a parabolic annular mirror or pair of parabolic mirrors, or a set of lenses or cut lenses. The direction-changing elements change the resonance path from a normal direction at the partially reflective surface 3A (or surfaces when a three-mirror configuration is employed). Polarized illumination light 10 is introduced at a first region of partially reflective surface 3A, is changed in direction by direction-changing element 12B, and is optionally focused by a lens or lens system 15B onto surface of interest 1. Lens/focusing system 15B and direction changing element 12B may be provided by a single element, such as a hemispherical proximity lens, that performs both function as shown for some embodiments in the above-referenced U.S. patent application. On the other side of the resonance path from the intersection with surface of interest 1, another optional focusing element 15A and direction changing element 12A restore the reflected beam to essentially the same shape and state as the beam entering the resonator. Polarizing element 2 can be located on either the entry or the exit (e.g., location 2A) from partially reflective surface 3A, or actually anywhere along the resonance path.

Light from illumination source 10 may be linearly or circularly polarized so that linearly or circularly polarized light is striking the surface of interest, depending on measurement needs. It should be noted that the type of polarization striking surface of interest 1 is dependent both on the polarization of light provided from illumination source 10 and the position of polarizing element 2, as if polarizing element 2 is introduced between surface of interest and illumination source 10, then the type of polarization (i.e., linear or circular) will be changed by polarizing element 2 before the light reaches surface of interest 1.

One or more detectors 11, 11A are locate on the far side of the resonator from illumination source 10 (transmission end) and one or both of the transmission 6B (dark field) or reflection 6A (bright field) patterns can be observed. The effect of polarizing element 2 on sensitivity is the same as that described above: two trips are required between partially-reflective surface 3A for a ray to interfere with itself, and therefore sensitivity of the resonator is increased. Since the dual angle configuration already has a doubled sensitivity over a standard Fabry-Perot resonator, as pointed out in the above-referenced U.S. patent application and due to the dual path between surface of interest 1 and partially reflective surface 3, the total result is quadrupled sensitivity for the depicted embodiment over a standard Fabry-Perot resonator with parallel plates.

Figure 6:
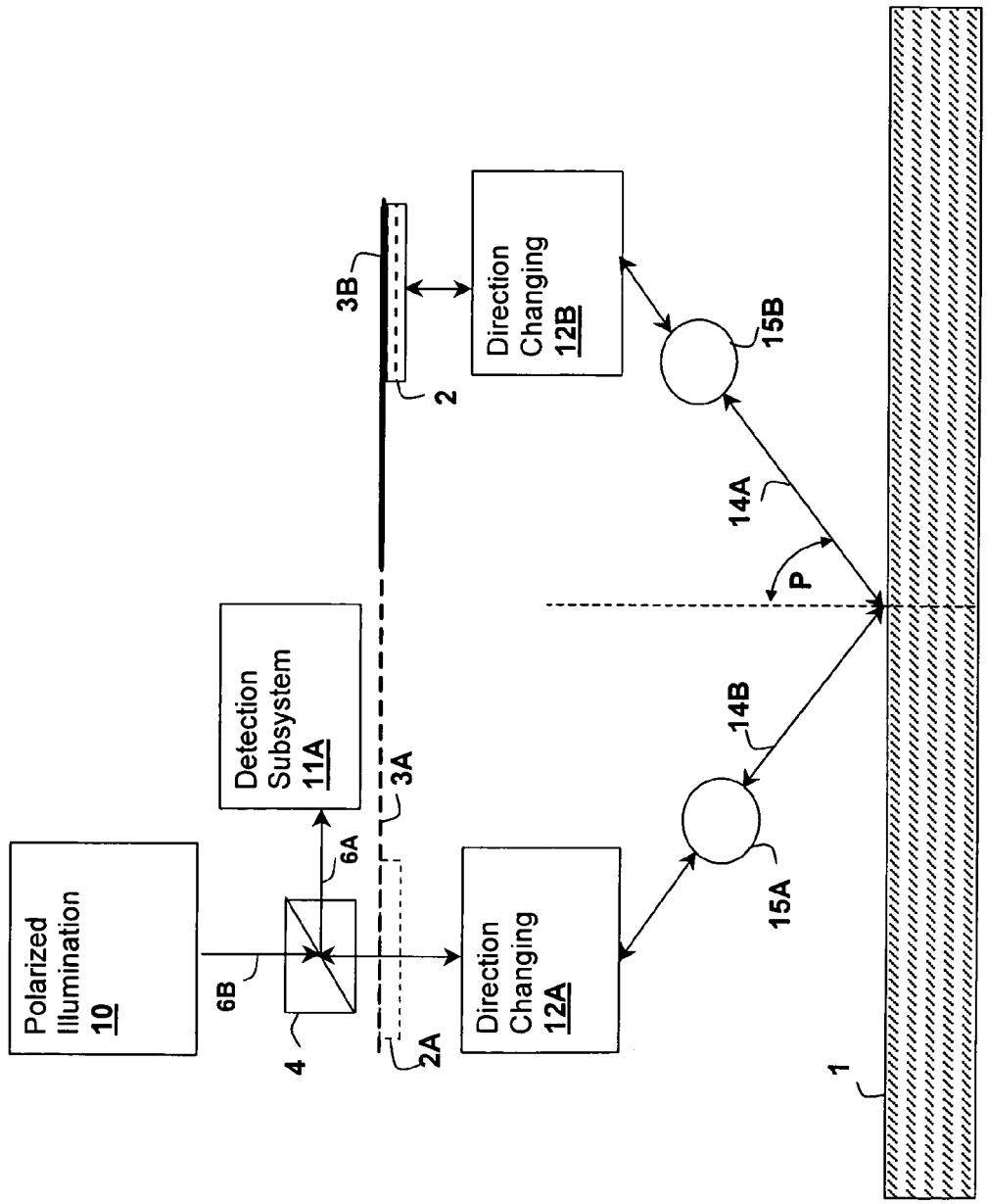

FIG. 6 shows an alternative embodiment of the optical system of FIG. 5 that has a higher finesse due to the incorporation of a fully reflective (and thus less lossy) region 3B on the plate that includes partially reflective surface 3A. In the depicted embodiment, the illumination must be provided and the detection must be taken at one end due to the opaqueness of fully reflective region 3B, but polarizing element 2 may still be located at location 2 or 2A or an other suitable point in the resonance path.

Figure 7:
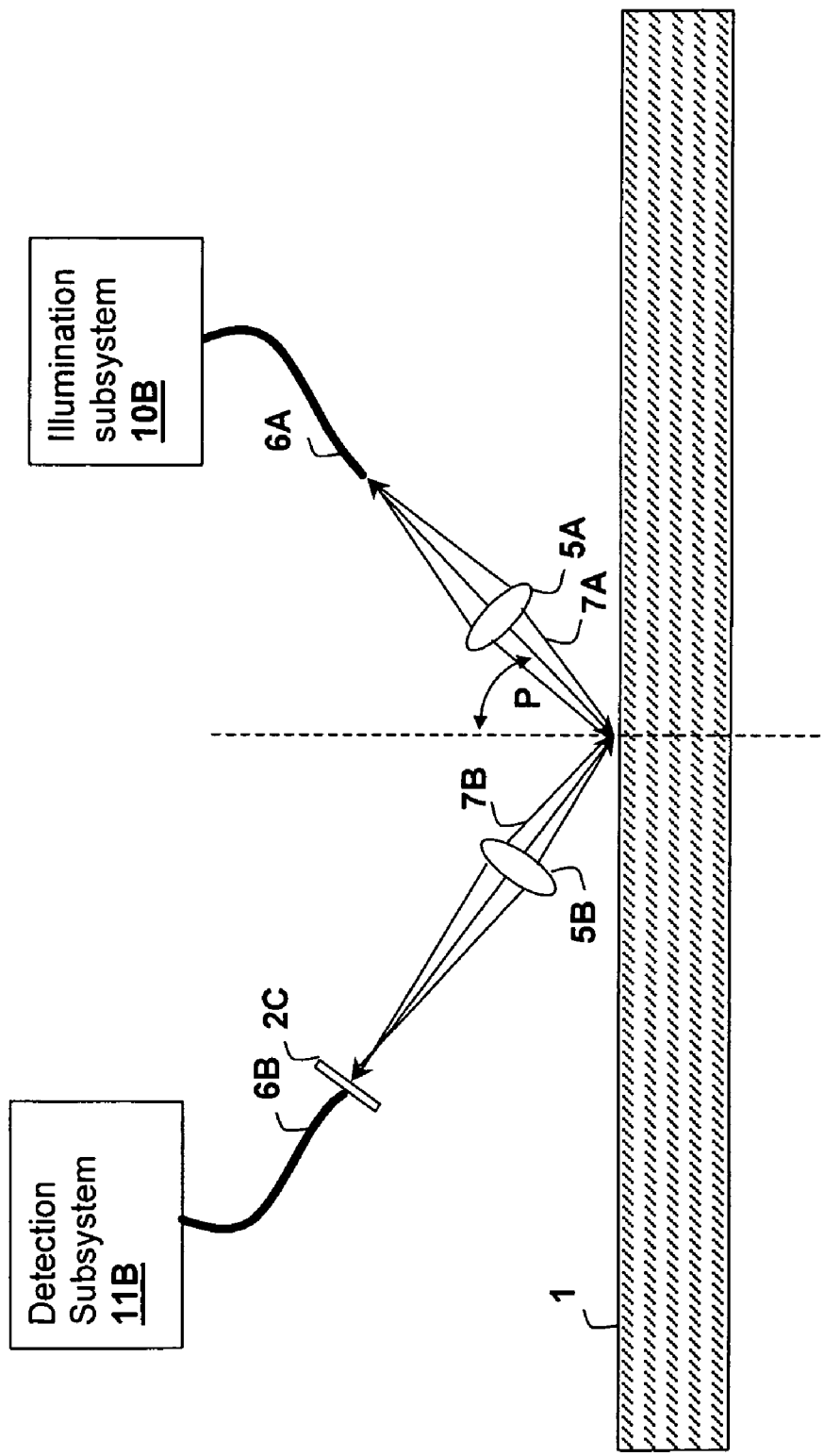

FIG. 7, shows an optical system in accordance with another embodiment of the present invention. The system of FIG. 7 is illustrative of a system in which a point illumination source and a point detector are imaged onto surface of interest 1 by a pair of imaging lenses 5A and 5B (finite conjugation ratio) focused on surface of interest at an angle of incidence other than normal. The point source and point detectors can be provided, as shown, by a pair of polarization-preserving optical fibers 6A, 6B that couple their respective subsystem (illumination subsystem 10B and detection subsystem 11B) directly to the resonator. (Fiber 6A may be a standard fiber if a polarizing element is provided before partially reflective surface at the end of the fiber so that polarized light is introduced to the resonator. Similarly, a polarizing element located at the receiving fiber 6B and past the partially reflective coating can be used to select one polarization, and then intensity only may be measured as communicated through a standard fiber to detection subsystem 11B.

Optical fibers 6A, 6B have distal ends ground and coated with a partially reflective coating, so that the Fabry-Perot resonator is formed between the faces at the distal ends of optical fibers 6A, 6B. A polarizing element 2C may be incorporated as part of the coating at the end of one of fibers 6A, 6B or may be provided as a discrete element. A polarizing beam-splitter can be included within detection subsystem 11B to select between the polarizations, and optionally a second detector can be included in detection subsystem 11B, thus selecting one or both resonance profiles (bright field, dark field or both).

Imaging beams 7A and 7B intersect at a point on surface of interest 1 for which the length is resonant. Any misalignment of the focal axes of imaging lenses 5A and 5B, results only in a shift of the point of intersection of beams 7A and 7B to a point where the resonance is supported. Just as in the above-described embodiment of FIGS. 4, 5, and 6, the embodiment of FIG. 7 has a quadrupled sensitivity over a standard Fabry-Perot resonator.

While the point source/point detector embodiment has disadvantages in that the mirror (fiber end) quality must be very high, the use of such a system is very advantageous in that no collimator is required to produce a small spot size, no separate mirrors are required to form the Fabry-Perot resonator, thus reducing the number of positioning variables in the system. The reduction in complexity and weight is also advantageous for scanning and data storage/retrieval device applications.

It should be understood for all of the above embodiments that the used of illustrative rays to indicate a resonant path illustrates only a single ray of an image. Incorporation of focusing elements may narrow the profile of the image at a particular surface, but multiple resonant paths exist and the resonance is supported by multiple pairs of points on one or more partially or fully reflected surfaces, as long as the total path length around the resonator is resonant (i.e., an integral number of wavelengths) for that path. It should also be understood that since polarization can be altered by lenses, focusing systems and other "non-polarizing" components in the above-described optical system embodiments of the invention, measures should be taken to preserve the polarization of light passing through such elements by appropriate optical coatings or other means.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An optical system, comprising:
   an illumination system for providing a coherent beam for illuminating a surface of interest through a first partially reflective surface;
   at least one reflector including said first partially reflective surface for sustaining multiple internal reflections in a resonant cavity formed at least partially between said at least one reflector and said surface of interest, and wherein an extraction partially-reflective one of said at least one reflector permits light to exit said resonant cavity;
   a detector for detecting an intensity of light leaving said cavity through said extraction surface; and
   a polarizing element located within a resonant path within said resonator, wherein said polarizing element alters a polarization of light between a forward path and a reverse path of a ray through said resonant cavity, such that light traveling along said forward path prior to entering said polarizing element is orthogonal to light leaving said polarizing element along said reverse path.

2. The optical system of claim 1, further comprising a polarizing beam splitter positioned between said extraction partially-reflective surface and said detector for providing a single polarization of light to said detector, whereby a particular wavelength-dependent resonance profile at said detector is inverted by action of said polarizing element.

3. The optical system of claim 2, wherein said at least one reflector includes a second partially reflective surface, wherein said extraction partially reflective surface is said second partially reflective surface, and wherein said resonance profile has dark resonance peaks on a bright background representing a reflection resonance.

4. The optical system of claim 2, wherein said extraction partially reflective surface is said first partially reflective surface, and wherein said resonance profile has bright resonance peaks on a dark background representing a transmission resonance.

5. The optical system of claim 2, further comprising a second detector for receiving light from said polarizing beamsplitter having a polarization orthogonal to that of said single polarization of light, wherein said first detector and said second detector each detect a corresponding resonance profile having either bright resonance peaks on a dark background or dark resonance peaks on a bright background, whereby both of said profiles are measured.

6. The optical system of claim 1, further comprising a lens positioned within said resonator for imaging a region of said surface of interest on a first image and a second image at said at least one reflector, and wherein said polarizing element ensures that reflected rays of said first image are orthogonal to corresponding rays of said second image.

7. The optical system of claim 6, wherein said first image is an illumination image that receives said coherent beam from said illumination system and images said coherent beam on said region of said surface of interest.

8. The optical system of claim 7, wherein said lens has an infinite conjugation ratio and wherein said region is a diffraction-limited point on said surface of interest.

9. The optical system of claim 6, wherein said lens has a finite conjugation ratio and wherein said region is a diffraction-limited point on said surface of interest and wherein said first image and said second image are at least one diffraction-limited point on said at least one reflector.

10. The optical system of claim 1, further comprising:
a first direction-changing element positioned along said resonant path between said at least one reflector and said surface of interest for changing a direction of light leaving said at least one reflector from normal to said at least one reflector to said predetermined non-zero angle away from normal to said surface of interest; and
a second direction-changing element positioned along said resonant path between said at least one reflector and said surface of interest for changing a direction of light leaving said surface of interest to a direction normal to said at least one reflector, whereby a single ray travels four times within said optical system before interfering with itself.

11. The optical system of claim 1, further comprising an optical focusing system positioned along said resonant path between said first partially-reflective surface and an intersection between said surface of interest and said resonant path, wherein said optical focusing system alters an angle of incidence of said light from said resonant path normal to said first partially-reflective surface to a direction aligned along said predetermined non-zero angle with respect to said surface of interest.

12. The optical system of claim 11, wherein said at least one reflector includes a second partially reflective surface, wherein said extraction partially reflective surface is said second partially reflective surface, and further comprising a second optical focusing system positioned along said resonance path between said surface of interest and said second partially reflective surface, wherein said second optical focusing system further changes an angular direction of light leaving said surface of interest to a direction normal to said second partially-reflective surface.

13. The optical resonator of claim 11, wherein said extraction partially-reflective surface is said first partially-reflective surface, and wherein said optical focusing system comprises a single high-index focusing element positioned between said surface of interest and said first partially-reflective surface, wherein said high-index focusing element lies twice within said resonance path and thereby changes an angle of incidence of said resonance path from normal at intersections of said resonance path with said first partially-reflective surface to said predetermined non-zero angle at said surface of interest.

14. The optical system of claim 1, wherein said extraction partially-reflective one of said reflectors is said first partially-reflective surface.

15. The optical system of claim 1, wherein said at least one reflector further includes a second partially-reflective surface and wherein said extraction partially-reflective one of said reflectors is said second partially-reflective surface.

16. The optical system of claim 15, wherein said first partially reflective surface is a polished and coated end of a first optical fiber extending from said illumination system, and wherein said second partially-reflective surface is a polished and coated partially-reflective end of a second optical fiber extending to said detection system.

17. The optical system of claim 15, wherein said at least one reflector further includes a fully reflective surface in addition to said first partially-reflective surface.

18. The optical system of claim 17, wherein said fully reflective surface and said first partially reflective-surface are formed as a fully-reflective region and a partially-reflective region on the same surface.

19. The optical system of claim 1, wherein said at least one reflector is positioned at a predetermined non-zero angle with respect to said surface of interest, whereby light that leaves said at least one reflector on an optical path normal to said at least one reflector intersects said surface of interest at said predetermined non-zero angle away from normal at said surface of interest, and returns to said at least one reflector in a normal direction.

20. A method for optically detecting features on a surface of interest, said method comprising:
illuminating a partially-reflective surface with a coherent beam;
repeatedly reflecting coherent light in a cavity formed at least partially between said at least one partially-reflective surface and a surface of interest;
polarizing said reflected coherent light during each propagation through said cavity, whereby said reflections are twice polarized resulting in an orthogonal polarization change at an endpoint of said cavity to effectively double an optical length of said cavity;
detecting an intensity of light leaving said cavity at said at least one partially-reflective surface; and
determining characteristics of said features on said surface of interest in conformity with a result of said detecting.

21. The method of claim 20, further comprising imaging a first region of said surface of interest on a second region of said partially reflective surface with an imaging lens, thereby improving a resolution of said detecting, and wherein said polarizing reduces interference between said illuminating coherent beam and said reflections at said partially reflective surface.

22. An optical system, comprising:
- an illumination system for providing a coherent illumination beam;
- at least one reflector including at least one partially reflective surface for sustaining multiple internal reflections of said coherent illumination beam in a cavity formed at least partially between said at least one reflector and a surface of interest;
- means for altering a polarization of light within said cavity so that light returning upon reflection from said at least one partially reflective surface to said at least one reflector is polarized orthogonally to the same light that left the at least one partially reflective surface, whereby an optical length of said cavity is doubled.

* * * * *